(12) United States Patent
Biedermann et al.

(10) Patent No.: US 9,592,064 B2
(45) Date of Patent: Mar. 14, 2017

(54) TARGETING DEVICE FOR GUIDING A DRILL ARRANGEMENT

(71) Applicants: Lutz Biedermann, VS-Villingen (DE); Wilfried Matthis, Weisweil (DE); Tobias Hägle, Donaueschingen (DE); Kaj Klaue, Savosa (CH)

(72) Inventors: Lutz Biedermann, VS-Villingen (DE); Wilfried Matthis, Weisweil (DE); Tobias Hägle, Donaueschingen (DE); Kaj Klaue, Savosa (CH)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 265 days.

(21) Appl. No.: 14/080,782

(22) Filed: Nov. 14, 2013

(65) Prior Publication Data
US 2014/0142582 A1    May 22, 2014

Related U.S. Application Data

(60) Provisional application No. 61/726,358, filed on Nov. 14, 2012.

(30) Foreign Application Priority Data

Nov. 14, 2012 (EP) .................................... 12192679

(51) Int. Cl.
*A61B 17/17* (2006.01)

(52) U.S. Cl.
CPC .......... *A61B 17/17* (2013.01); *A61B 17/1717* (2013.01); *A61B 17/1739* (2013.01); *A61B 2017/1775* (2013.01)

(58) Field of Classification Search
CPC . A61B 17/16; A61B 17/1613–17/1633; A61B 17/1662–17/1669;
(Continued)

(56) References Cited

U.S. PATENT DOCUMENTS 550,783 A * 12/1895 Elliott ..................... E21B 7/068
                                                       175/75
2,960,892 A * 11/1960 Spravka .................. B23B 5/365
                                                       408/127
(Continued)

FOREIGN PATENT DOCUMENTS

CN          1184409 A     6/1998
CN        102292037 A    12/2011
(Continued)

OTHER PUBLICATIONS

European Search Report and Opinion issued by the EPO for EP 12192679.4 on Feb. 18, 2013 (4 pages).
(Continued)

*Primary Examiner* — Christian Sevilla
*Assistant Examiner* — Eric S Gibson
(74) *Attorney, Agent, or Firm* — Lewis Roca Rothgerber Christie LLP (57) ABSTRACT

A targeting device for guiding a drill arrangement for forming an arc-shaped bore in an assembly of adjacent bones or bone fragments, comprises a support frame, a pivoting device mounted to the support frame and arranged to receive the drill arrangement and to allow a pivoting movement of the drill arrangement along an arc-shaped path having a predetermined radius of curvature $r_c$ around a pivot axis. The support frame is provided with at least three fixation devices each configured to fix a bone or bone fragment of the bone assembly to define a fixed position in space of the bone assembly with respect to the pivoting device when the bone assembly is installed on the support frame.

24 Claims, 8 Drawing Sheets

(58) Field of Classification Search
CPC . A61B 17/17–17/1767; A61B 17/1796; A61B 2017/1771–2017/1792
USPC .......................................................... 606/96
See application file for complete search history.

(56) References Cited

U.S. PATENT DOCUMENTS

| | | | | |
|---|---|---|---|---|
| 5,017,057 | A * | 5/1991 | Kryger | B23B 5/365 408/127 |
| 6,607,530 | B1 * | 8/2003 | Carl | A61B 17/15 606/279 |
| 8,092,495 | B2 * | 1/2012 | Boulis | A61B 17/0206 604/116 |
| 8,419,744 | B2 * | 4/2013 | Petit | A61F 2/4611 606/99 |
| 2002/0165551 | A1 * | 11/2002 | Trnka | A61B 17/1739 606/86 R |
| 2005/0234449 | A1 * | 10/2005 | Aferzon | A61B 17/7089 606/86 A |
| 2005/0267481 | A1 | 12/2005 | Carl et al. | |
| 2005/0273167 | A1 * | 12/2005 | Triplett | A61B 17/1757 623/17.11 |
| 2006/0149278 | A1 * | 7/2006 | Abdou | A61B 17/7077 606/90 |
| 2008/0255563 | A1 * | 10/2008 | Farr | A61B 17/025 606/79 |
| 2008/0287950 | A1 * | 11/2008 | Frigg | A61B 17/1717 606/62 |
| 2009/0069846 | A1 * | 3/2009 | Bull | A61B 17/0469 606/228 |
| 2009/0099571 | A1 * | 4/2009 | Cresina | A61B 17/17 606/96 |
| 2009/0149861 | A1 * | 6/2009 | Brodsky | A61B 17/1725 606/96 |
| 2009/0187191 | A1 * | 7/2009 | Carl | A61B 17/1642 606/80 |
| 2010/0137924 | A1 * | 6/2010 | Tuke | A61B 17/175 606/86 R |
| 2010/0160925 | A1 * | 6/2010 | Heilala | A61B 17/17 606/96 |
| 2010/0268237 | A1 * | 10/2010 | Carl | A61B 17/1631 606/87 |
| 2010/0292722 | A1 | 11/2010 | Klaue | |
| 2011/0282397 | A1 * | 11/2011 | Richter | A61B 17/1682 606/304 |
| 2012/0109217 | A1 * | 5/2012 | Perineau | A61B 17/1725 606/301 |
| 2012/0277745 | A1 * | 11/2012 | Lizee | G01B 5/24 606/59 |
| 2013/0030446 | A1 * | 1/2013 | Wayne | A61B 17/1739 606/104 |
| 2013/0325076 | A1 * | 12/2013 | Palmer | A61B 17/1739 606/318 |
| 2014/0142575 | A1 * | 5/2014 | Biedermann | A61B 17/846 606/62 |
| 2014/0142582 | A1 * | 5/2014 | Biedermann | A61B 17/1739 606/96 |
| 2014/0214095 | A1 * | 7/2014 | Rosenwasser | A61B 17/66 606/301 |
| 2014/0343556 | A1 * | 11/2014 | Valenti | A61B 17/1739 606/87 |
| 2015/0100099 | A1 * | 4/2015 | Kitagawa | A61B 17/3403 606/86 A |

FOREIGN PATENT DOCUMENTS

| | | |
|---|---|---|
| WO | WO 96/36284 A1 | 11/1996 |
| WO | WO 2007/125279 A2 | 11/2007 |
| WO | WO 2008/099176 A1 | 8/2008 |
| WO | WO 2010/085538 A2 | 7/2010 |
| WO | WO 2011/072249 A1 | 6/2011 |
| WO | WO 2011/133407 A2 | 10/2011 |

OTHER PUBLICATIONS

CN Office action dated Nov. 2, 2016 for Application No. 201310556203.4 (6 pages).

* cited by examiner

TARGETING DEVICE FOR GUIDING A DRILL ARRANGEMENT

CROSS-REFERENCE TO RELATED APPLICATIONS

The present disclosure claims the benefit of U.S. Provisional Patent Application Ser. No. 61/726,358, filed Nov. 14, 2012, the contents of which are hereby incorporated by reference in their entirety, and claims priority from European Patent Application EP 12192679.4, filed Nov. 14, 2012, the contents of which are hereby incorporated by reference in their entirety.

BACKGROUND

Field of the Invention

The invention relates to a targeting device for guiding a drill arrangement for forming an arc-shaped bore in an assembly of adjacent bones or bone fragments, respectively.

Description of Related Art

From document WO 2011/072249 A1, a guidewire targeting device for assisting in the arthrodesis of the heel is known that allows the formation of two straight cutting paths starting from a bottom section of the calcaneus and extending through the talus towards the tibia canal using guide wires, which are angled relative to each other. Using a drill and a reamer after removing the targeting device, a bent bore or canal may be established from a combination of paths that may receive an immobilizing nail. Tubular sleeves are used in the targeting device to guide the wires straight through the bone material.

This approach, however, suffers from an increased damage of bone material as two cutting paths are created. Further, the patient may suffer from pain when the bottom portion of the calcaneus is involved in the surgical process. Moreover, duration and stability of the overall configuration may not be satisfactory. Therefore, in some surgical applications, a further need for forming bores in bone material departing from the commonly applied straight shape has arisen in the recent past.

Some of those applications relate to drilling arc-shaped bores into a bone or an assembly of multiple adjacent bones.

A device for forming an arcuate channel in vertebrae has, for example, been proposed in US 2005/0267481 A1, wherein two path-guard members connected with each other via a platform assembly are attached to each one vertebra by multiple nails, respectively. A pivot arm mounted at the platform holds an arc-shaped tube member through which a drive cable extends that is driven by a motor such as to rotate a drill bit arranged at a front end of the tube member. Due to the arcuate shape of the tube an arc-shaped bore hole can be drilled when the pivot arm is advanced towards the bone. In this manner, an intervertebral disk can be directly accessed through the arc-shaped bore that is cut into adjacent vertebral bodies and through respective end faces thereof.

Another device for forming a bore in an arcuate shape is described in US 2010/0292722 A1. The device comprises a main body attached to the heel of the human body by means of Kirschner-wires, and an arc-shaped guide enables guiding a tube having a corresponding radius of curvature $r_c$ to perform a pivoting movement. The device is attached to the heel at two locations. A drill bit driven by a motor via a drive cable extending through the tube enters into the calcaneus first, and then advances the arcuate-shaped bore through the talus into the marrow space of the tibia. The circular arc-shaped bore thus formed allows inserting a corresponding nail which immobilizes the bones involved.

SUMMARY

It is an object to provide a targeting device, which improves the accuracy of a drilling process, or which allows a more accurate control of the same.

An embodiment of the targeting device provides for at least three different fixation devices, which each allow fixation of a single bone or bone fragment of a bone assembly. The fixation devices are mounted on a common frame. A pivoting device is also provided and is configured to be mountable on the frame. The pivoting device holds a drill arrangement and allows advancement of the drill arrangement by a pivoting movement that is performed along an arc-shaped path within a plane.

In this embodiment, the position of the bone assembly is completely defined by fixation at three points in space due to the three fixation devices. As a consequence, an arc-shaped path along which drilling takes place by virtue of the pivoting movement of the drill arrangement is fixed relative to the bone assembly. Hence, no deviations such as drifting or the like may occur and the accuracy of the arc-shaped bore is improved. This may be important when an arc-shaped nail is inserted after fixation by the three fixation devices, which is designed to immobilize the bone assembly, and when the shape of the arc-shaped nail has to correspond to the arc-shape of the bore.

In one specific embodiment, the targeting device comprises a drill jig. The drill jig has a jig portion which allows it to indicate a position of the arc-shaped bore before, during or after drilling, The drill jig may be provided as a separate part from the pivoting device, or may also be formed connected with the pivoting device. The drill jig may pivot around a same pivot axis as the pivoting device. In one specific embodiment, the drill jig and the pivoting device may be provided as separate parts removable from the frame, wherein one part is replaced by the other during use of the targeting device.

BRIEF DESCRIPTION OF THE DRAWINGS

Further features and advantages of the invention will become apparent from the description of an embodiment by means of the accompanying drawings. In the drawings.

DETAILED DESCRIPTION

Figure 1:
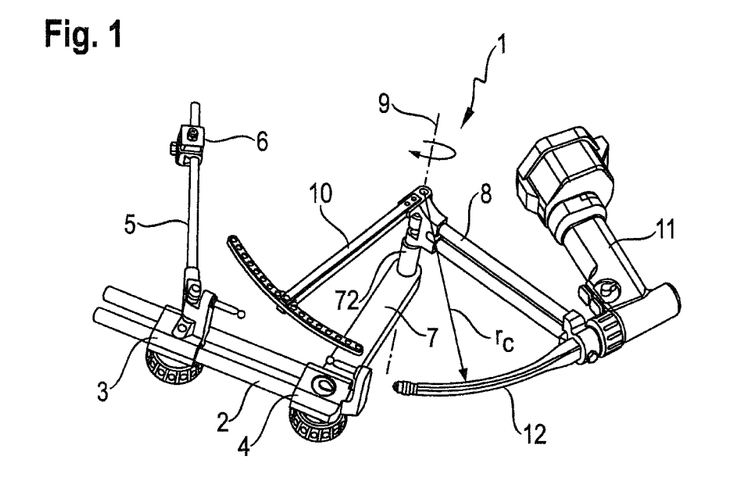
FIG. 1 shows a perspective view of an overview of a targeting device according to a specific embodiment and with a drill arrangement.

An embodiment of a targeting device 1 that holds and guides a drill arrangement 11, 12 is shown in FIG. 1. The assembly shown in FIG. 1 is specifically designed for drilling circular arc-shaped bores through bones of the heel of the human body. The application is designed particularly to perform arthrodesis of the hindfoot. Similar arrangements may be configured for application to other parts of the human body without departing from the scope of the appended claims.

Figure 15:
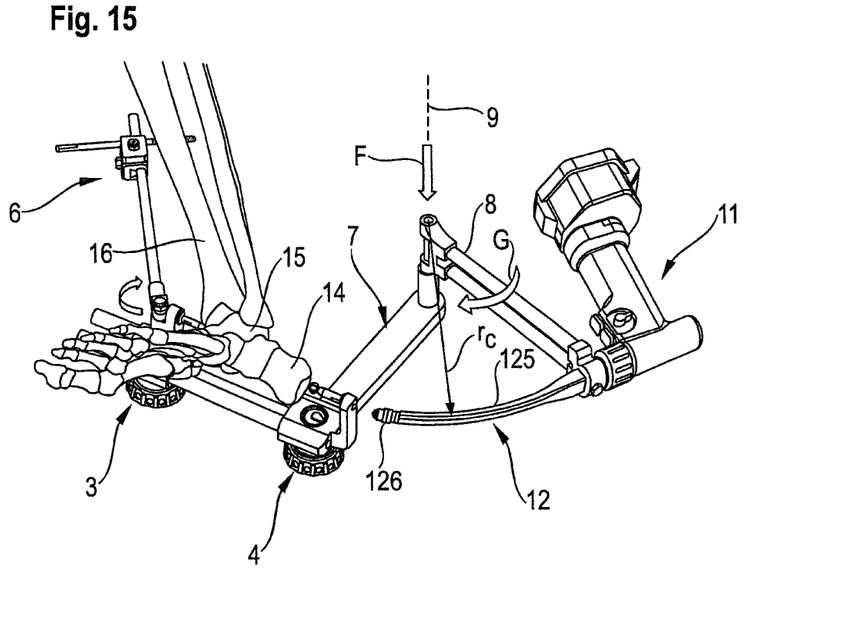
FIG. 15 shows a further step of replacing the drill jig and attaching the pivoting arm and the drill arrangement to the pivot axis of the targeting device.
Figure 16:
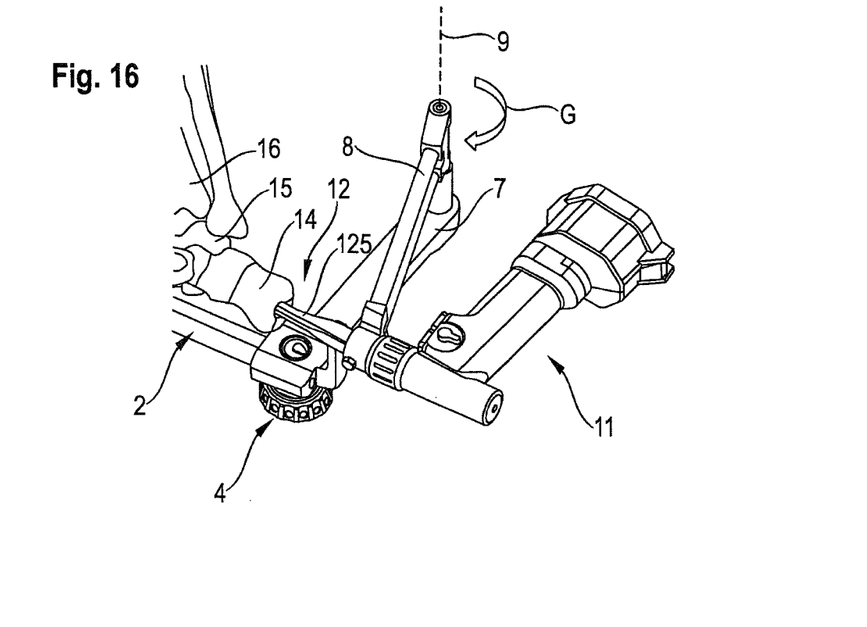
FIG. 16 shows a further step of advancing a drill bit and circular arc-shaped tube of the drill arrangement into the bore by pivoting the pivoting device.
Figure 17:
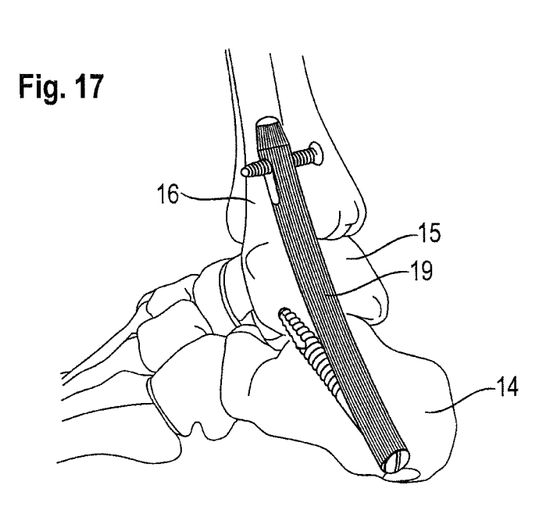
FIG. 17 shows an example of a circular arc-shaped bone nail inserted into the bore formed according to the method of using the targeting device.

FIG. 1 provides an overview of the targeting device, details of its components are shown in FIGS. 2 through 7, and steps for preparing the human foot and heel, for using the targeting device and for operating the drill assembly are shown in FIGS. 8 through 16. A bone nail compatible and insertable into the bore drilled using the drill arrangement according to FIGS. 1-7 and the method according to FIGS. 8-16 is shown in FIG. 17.

In FIG. 1, the targeting device 1 includes a frame or framework which basically comprises a main support 2 with a first pivotable support portion 5 and a second pivotable support portion 7. The main support 2 is further configured to receive first and second fixation devices 3, 4 and the first pivotable support portion 5 is configured to receive a third fixation device 6 (see also FIGS. 13 and 14).

The targeting device 1 of this embodiment further includes a pivoting device 8 that is adapted to hold a drill tool 11 and a circular arc-shaped tube portion 12 with drill bit. The pivoting device 8 can be attached to a rotational support 72 on the second pivotable support portion 7. The rotational support 72 defines a pivot axis 9 that is—in this specific embodiment—substantially perpendicular to a plane spanned by parts 2, 5 and 7. A rotatable drill jig 10 may also be attached to the rotational support 72 of the second pivotable support portion 7. In FIG. 1, pivoting device 8 and drill jig 10 are indicated as an integral part. Due to the above construction, the planes in which the pivoting device 8, the drill arrangement 11, 12 and the drill jig 10 rotate, are substantially parallel to the plane spanned by the frame parts 2, 5 and 7.

Figures 11, 12A, 12B:
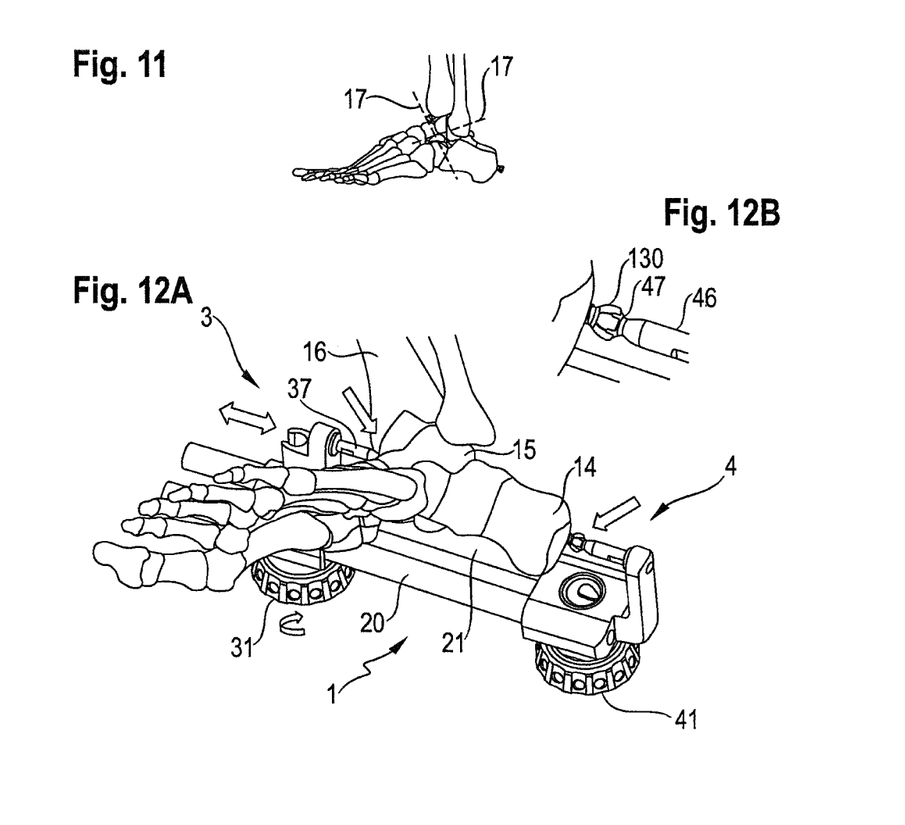
FIG. 11 shows a further step of using the targeting device in a perspective view of the human foot wherein in a schematic representation (dashed lines) Kirschner-wires are inserted to reposition bones of the heel.
FIG. 12A shows a further step of using the targeting device wherein the human foot is installed on the main support with the first and second fixation (soft tissue parts not shown)
FIG. 12B shows an enlarged view of a connection established between a tulip head of the bone anchor and a ball head protruding from a tip of a pin provided at the first fixation device.
Figure 13:
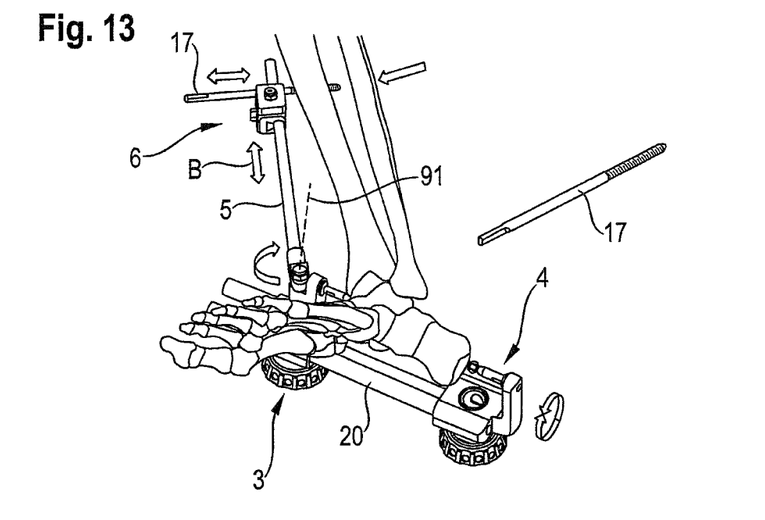
FIG. 13 shows a further step of using the targeting device wherein the first pivotable support portion with the third fixation device is mounted to the main support, and the fixation device is fixed at the tibia.

As shown in FIGS. 12A and 13 which is described in more detail below, the fixation devices 3, 4 and 6 are designed to be fixed at bones or bone fragments of the bone assembly of the heel, for example, in this specific embodiment, a calcaneus 14 (fixation device 4), a talus 15 (fixation device 3) and a tibia 16 (fixation device 6). In order to meet the specific anatomy of the respective heel, the fixation devices 3 and 4 can be slidably adjusted in a linear fashion with respect to each other, and the third fixation device 6 may also be slidably adjusted on the first pivotable support portion 5. Further, the third fixation device 6 can be rotated with respect to the position of the other two fixation devices 3, 4 by rotating the first pivotable support portion 5.

Figure 4A:
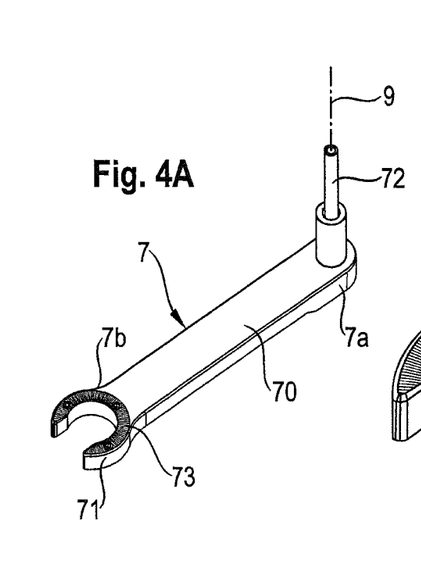
FIG. 4A shows in a perspective view details of the second pivotable support portion as shown in FIG. 1 attached to the second fixation device.

On the right side of the targeting device 1, the second pivotable support portion 7 can also be rotated with respect to the main support 2, wherein the second pivotable support portion 7 provides at an end section 7a, opposite to an end section 7b connected to the main support 2 as shown in FIG. 4A, for the rotational support 72 which defines the pivot axis 9 for the pivoting device 8 with the drill arrangement 11, 12 or the drill jig 10.

Figure 5:
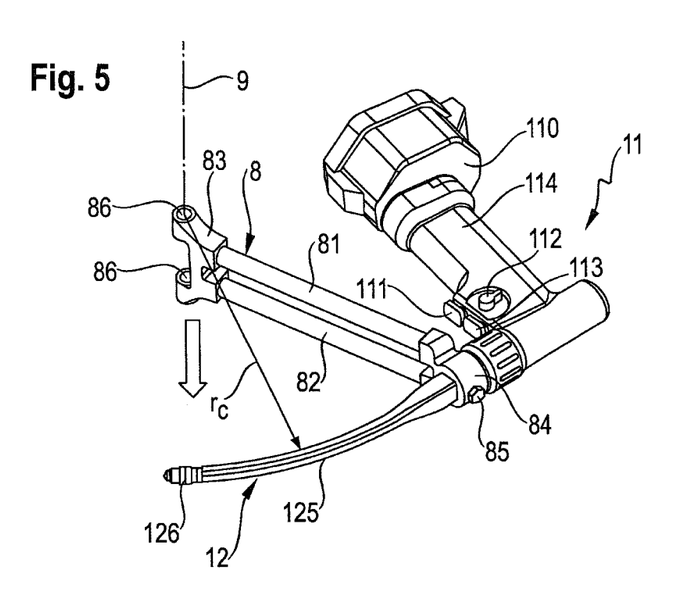
FIG. 5 shows in a perspective view details of the pivoting device and the drill arrangement as shown in FIG. 1.

The drill arrangement 11, 12 comprises the drill tool 11 and the tube portion 12 with drill bit 126 that is received and held by the pivoting device 8 (see also FIG. 5). The tube portion 12 is circular arc-shaped as shown in FIG. 1. The tube portion 12 has a radius of curvature $r_c$, which corresponds to its distance from the pivot axis 9 such that when the pivoting device 8 is rotated about pivot axis 9, the tube portion 12 moves along its own curved central axis. As a consequence, when a user adjusts the rotation angle of the second pivotable support portion 7 with respect to the main support 2, a circular or circular segment path described by the movement of the tube portion 12 and the drill bit 126 can be positioned relative to the bone assembly of the heel of the patient, as will be described in more detail with reference to FIG. 14 below.

Figure 2:
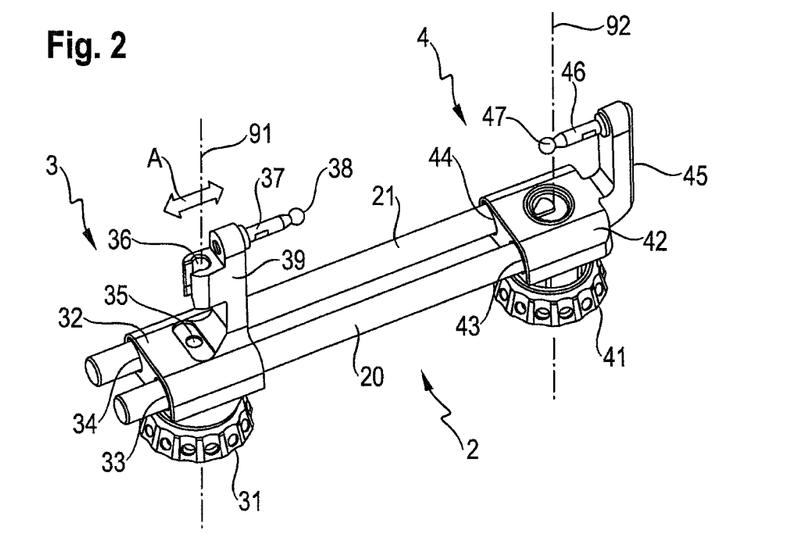
FIG. 2 shows in a perspective view details of the main support with first and second fixation devices as shown in FIG. 1.

The individual components of the targeting device 1 and the drill arrangement 11, 12 are shown in more detail in FIGS. 2 through 6. FIG. 2 shows details of the main support 2. The main support 2 of this specific embodiment comprises guide rails 20, 21 which are arranged in parallel. At one end of the guide rails 20, 21, the first fixation device 3 is arranged and at the other end the second fixation device 4 is arranged. The first fixation device 3 is slidable while the second fixation device 4 is fixed on the guide rails 20, 21. Nevertheless, other embodiments may also allow for both fixation devices 3, 4 to be slidable.

The second fixation device 4 comprises a (fixed) carriage 42, which has a pinch wheel 41, a vertical part 45 extending vertically from a base part of the carriage 42, a pin 46 which protrudes horizontally from the vertical part 45 and a ball head 47 arranged at the tip of the pin 46. The pinch wheel 41 is arranged at the bottom of the carriage 42 and is configured to clamp or pinch the end section 7b with a C-shaped receiving portion 71 and a pattern of miniature ribs 73, described below with reference to FIGS. 4A and 4B.

The pinch wheel 41 may be rotated with respect to a cylindrical portion (not shown) having a thread cooperating with an inner thread provided at the pinch wheel 41 and defining a vertically extending axis 92 such as to increase or decrease its distance from a bottom face of the carriage 42. Manual fine adjustment of the pinch wheel 41 allows for a desired tactile response due to the pattern of miniature ribs 73 provided at the side of the second pivotable support portion 7, when the latter is rotated around vertical axis 92. A pattern of miniature ribs (not shown) arranged to cooperate with ribs 73 at the second pivotable support portion 7 may also be provided at the bottom face of the carriage 42. Further tightening of the pinch wheel 41 then allows a final locking of the orientation of the second pivotable support portion 7, when the ribs on both sides securely engage the corresponding grooves between the ribs on the other side.

Figure 7:
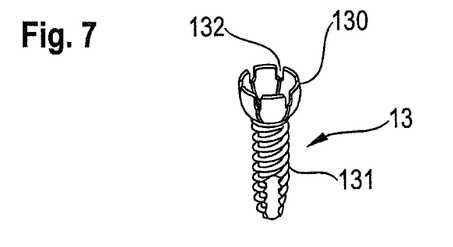
FIG. 7 shows in a perspective view details of a bone anchor having a tulip head as used in connection with the targeting device of FIG. 1.

The carriage 42 includes holes 43, 44 for receiving the guide rails 20, 21, respectively, and also has the vertical part 45, the horizontal pin 46 and the ball head 47 at its tip to facilitate fixing a part of a bone, more specifically the calcaneus 14. The pin 46 and ball head 47 form a receiving portion of the second fixation device 4. Thereby, the ball head 47 is configured to interact with a tulip head 130 of a bone anchor 13 that is shown in FIG. 7. Such a bone anchor 13, for this purpose, is anchored in the calcaneus 14 by virtue of its threaded shaft 131. The ball head 47 may snap into the tulip head 130 which has a resilient upper edge portion due to notches 132.

The connection between the ball head 47 and the tulip head 130 is one of the fixation points (out of at least three) between the targeting device 1 and the bone assembly. In this specific embodiment, the ball-joint-like connection established by the second fixation device 4 as described above provides for some small degree of freedom for polyaxial orientation of the components with respect to each other (as long as less than three fixation points have yet been established) eventually leading to the fixation of the bone assembly in three dimensional space.

As shown in FIG. 2 the first fixation device 3 is slidably arranged on guide rails 20, 21. Sliding adjustment and fixation of a position is accomplished by screw 35. Similar to the second fixation device 4, the first fixation device 3 has a carriage 32 with a pinch wheel 31, a vertically extending part 39, a horizontally protruding pin 37 and a ball head 38 at its tip. The function of ball head 38 is the same as in case of ball head 47 of the second fixation device 4. The pin 37 and ball head 38 form a receiving portion of the first fixation device 3. As shown in FIG. 12A, the pins 37, 46 protrude horizontally towards end faces of the talus 15 and calcaneus 14, respectively, when the human foot is installed on the main support 2. Sliding of the carriage(s) 32, 42 allows the ball heads 38, 47 to contact respective tulip heads 130 (see also FIG. 8) of anchors 13 anchored into the bone, respectively.

Figure 3:
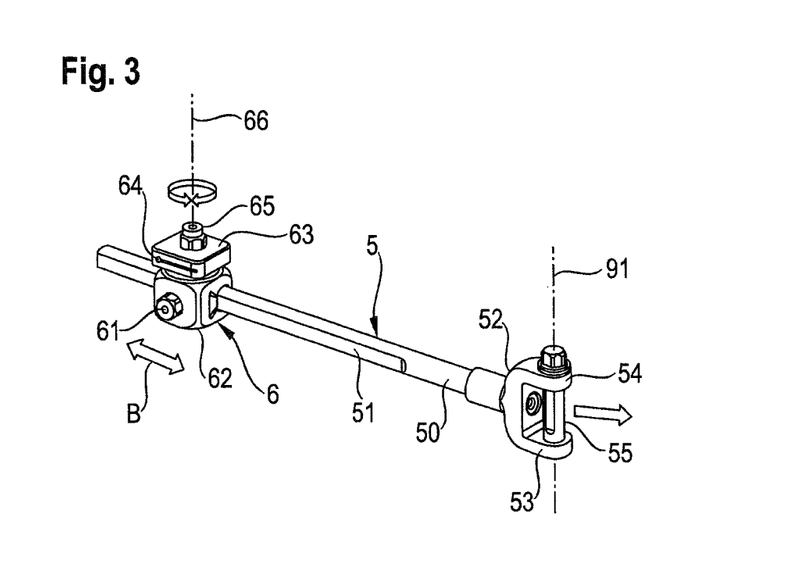
FIG. 3 shows in a perspective view details of the first pivotable support portion as shown in FIG. 1 attached with a third fixation device.

As shown in FIGS. 2 and 3, a guide 36 defines a joint axis and is designed to receive a pin 55 of the first pivotable support portion 5. The carriage 32 is provided with holes 33, 34 for receiving respective guide rails 20, 21 to allow the sliding adjustment along directions A.

FIG. 3 shows the first pivotable support portion 5, which in this embodiment comprises an elongated rod 50, which is attached to the first fixation device 3 by means of a joint 52 attached to one end of the rod 50. The joint 52 has two protruding parts 53, 54 provided with holes through which the pin 55 extends. Pin 55 is adapted to be received by guide 36 of the first fixation device 3. The pin 55 may have one or two threads in order to be held in place when installed in the guide 36. The pin 55 and the guide 36 define a vertical axis 91 of rotation around which the elongated rod 50 may pivot. The vertical axis 91 or the vertical axis 92, or both axes, according to this embodiment, are parallel to pivot axis 9, but other inclined configurations may be envisaged as well.

The elongated rod 50 has a flat portion 51 that allows for sliding adjustment of the third fixation device 6, wherein the flat portion 51 inhibits a rotation of the third fixation device 6 around a longitudinal axis of the rod 50. Further, the third fixation device 6 basically comprises a carriage 62 and a screw 61, which fixes the position of the third fixation device 6 along the longitudinal axis of the rod 50.

The third fixation device 6 further has a receiving part 63 including a cylindrical opening 64 configured to receive a portion of a Schanz screw 17, as shown in FIG. 13, for example. The Schanz screw 17 is inserted into the tibia 16. The fixation of the Schanz screw 17 within the cylindrical hole 64 of the receiving part 63 is secured by a screw 65. This connection provides for the third and final fixation point between the bone assembly and the targeting device 1.

Sliding adjustment of the third fixation device 6 along the rod 50 is possible along direction B, shown in FIGS. 3 and 13.

FIG. 4A shows details of the second pivotable support portion 7, which allows the operator, for example a surgeon or others, to determine the center point or pivot axis 9 for the circular arc-shaped path of the tube portion 12 with drill bit 126 at the tip of tubular body 125. The second pivotable support portion 7 includes an elongate shaft member 70, the C-shaped receiving portion 71 at its one end section 7b, and the rotational support 72 protruding vertically at its other end section 7a. The C-shaped receiving portion 71 is adapted to engage a cylindrical portion of the second fixation device 4 arranged above the pinch wheel 41 and below the bottom face of the carriage 42, which part is not shown in detail in FIG. 2.

Figure 4B:
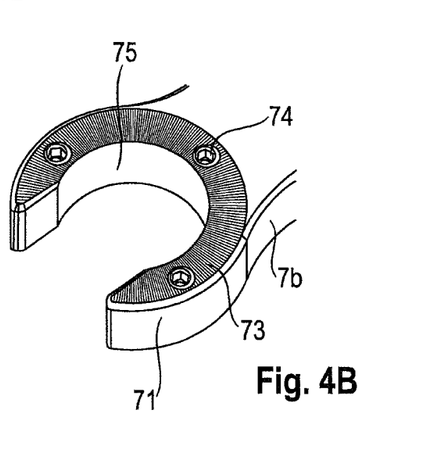
FIG. 4B shows an enlarged view of the C-shaped receiving portion of FIG. 4A with a pattern of ribs.
Figure 14:
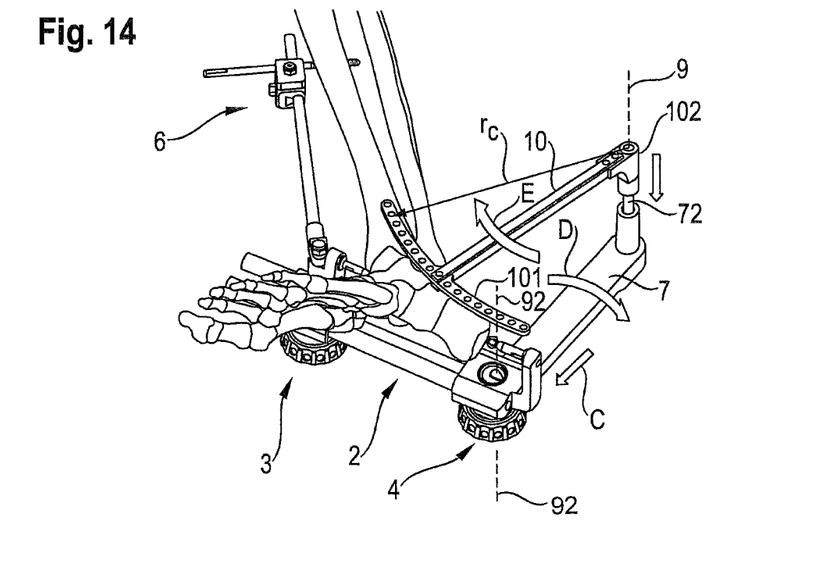
FIG. 14 shows a further step of using the targeting device wherein the drill jig and the second pivoting portion is swivelled to find an appropriate rotational position of the pivot axis defined at the second pivoting portion to drill the bore.

To allow a fine adjustment for the position of the pivot axis 9, miniature ribs 73 are provided on an upper surface of the C-shaped receiving portion 71 as shown in FIG. 4B, which offer a tactile response to the surgeon and also a more secure rotational adjustment of the second pivotable support portion 7. A locking mechanism provided at the second fixation device 4 allows for fixation of the elongate shaft member's position once it has been finally determined by the operating personnel, surgeon or any other staff, etc. Such determination is carried out using the drill jig 10 as shown in FIG. 14 and described with reference to FIG. 6 below.

FIG. 5 shows the pivoting device 8 and the drill arrangement with drill tool 11 and tube portion 12 with drill bit 126 in more detail. The pivoting device 8 comprises a joint part 83 with protruding parts protruding horizontally and holes 86 provided therein such as to be placed upon the pin-like rotational support 72 of the second pivotable support portion 7. As a consequence, the pivoting device 8 is restricted to a substantially horizontal pivoting movement around the pivot axis 9 with respect to the main support 2. Details of the movement and drilling process are depicted in FIGS. 15 and 16.

The pivoting device 8 is embodied with, for example, two parallel rods 81, 82 extending from the joint part 83. At the other end of the rods 81, 82, a ring 84 is integrally formed which is configured to hold and receive the tube portion 12 of the drill arrangement 11, 12. A screw 85 may secure the tube portion 12 to the pivoting device 8 when the tubular body 125 is received in the ring 84.

The tube portion 12 comprises the circular arc-shape tubular body 125 having a predetermined radius of curvature $r_c$, which corresponds to its distance from the pivot axis 9, i.e., the total length of the pivoting device 8 from the pivot axis 9 and joint 83 through rods 81, 82 up to the central axes of the ring 84 and of the tubular body 125, respectively. Pivoting of the pivoting device 8 moves the tube portion 12 along its own arc-shaped longitudinal central axis. The radius of curvature $r_c$ is in one specific embodiment equal to or larger than 130 mm and equal to or smaller than 240 mm, and—in further embodiments—more preferably equal to or larger than 140 mm, or equal to or larger than 150 mm, and/or more preferably equal to or smaller than 210 mm.

At the tip of the tube portion 12, the drill bit 126 that allows drilling into the bone material is provided. The drill bit 126 is driven via, e.g., a spiral drive cable that is configured to be rotated inside the tubular body 125. At the other end of the drive cable, an adaptor of the drill tool 11 is provided that transfers rotational motion from a motor (not shown) of the drill tool 11 to the drive cable. Details of a drill arrangement 11, 12 comprising a drill tool 11 and similar to that as used herein is described in detail in reference US 2010/0292722 A1, which is fully incorporated herein by reference.

A handle 114 of the drill tool 11 allows the surgeon to grip the drill tool and to advance it along with the pivoting device 8 such as to advance the drill bit 126 and the tube portion 12 into the calcaneus 14. Operation keys 111, 112 and 113 allow the surgeon to adjust the drill strength, moot and direction, respectively. Numeral 110 indicates a battery. The drill device 11 is shown as a cordless drill.

Figure 6:
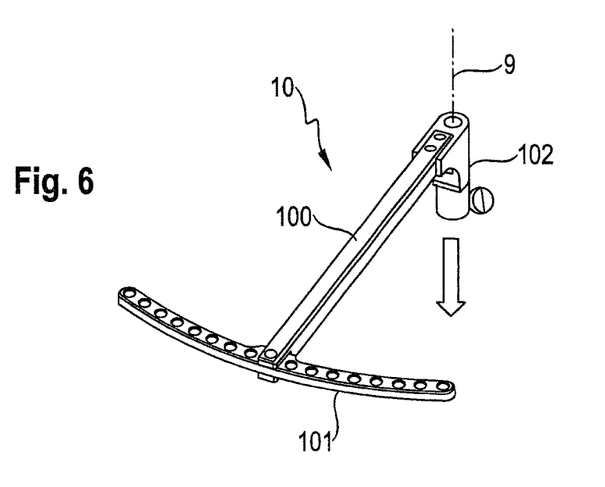
FIG. 6 shows in a perspective view details of a drill jig as shown in FIG. 1.

FIG. 6 shows the drill jig 10 which has a tubular section 102 that is vertically passed over the rotational support 72 of the second pivotable support portion 7. As noted above, drill jig 10 may be replaced by the pivoting device 8 during use, or may provided in addition to the same. Accordingly, the drill jig 10 has the same pivot axis 9 as the pivoting device 8 which holds the drill arrangement 11, 12. Moreover, the drill jig 10 has a horizontal arm 100, which has a length corresponding to that of the pivoting device 8, and a jig portion 101 provided at the end of the arm 100. The jig portion 101 is located above a position where the bore is to be drilled and is used to indicate the circular path that the bore will follow when the bore is drilled into the bone assembly below by the targeting device, as shown in FIG. 14. As a consequence, the circular arc-shaped jig portion 101 substantially pivots along the same circular path as the tube portion 12 with drill bit 126 and tubular body 125. This construction allows the surgeon to recognize the position of the bore to be drilled with respect to the bone assembly (herein: calcaneus, talus and tibia), and in response thereto, to reposition the shaft 7 and pivot axis 9, if corrections are needed.

It may be noted that the jig portion 101 is visible in an X-ray, and the targeting device may be used in conjunction with an X-ray tool to allow the surgeon to overlay the jig portion 101 onto the bones visible in the X-ray.

Figure 8:
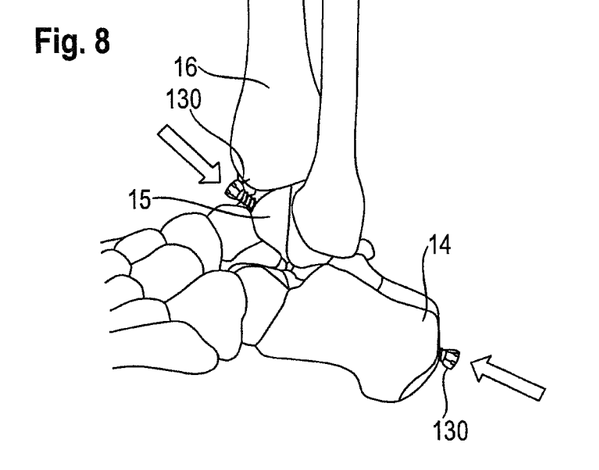
FIG. 8 shows a step of using the targeting device of FIG. 1 in a perspective side view of the heel with two bone anchors having a tulip head being inserted into the calcaneus and talus, respectively.

The method of using the targeting device 1 and drilling tool 11 is shown in FIGS. 8 through 16. A first step is shown in FIG. 8, wherein the heel to be immobilized is prepared and anchors 13 provided with tulip heads 130, in connection with FIG. 7, as described above are respectively fixed medially in the talus 15 and the calcaneus 14, respectively. It may be noted that the bone anchor 13 corresponding to the calcaneus 14 is inserted into an axial end face thereof, and not into a plantar end face thereof.

Figure 9:
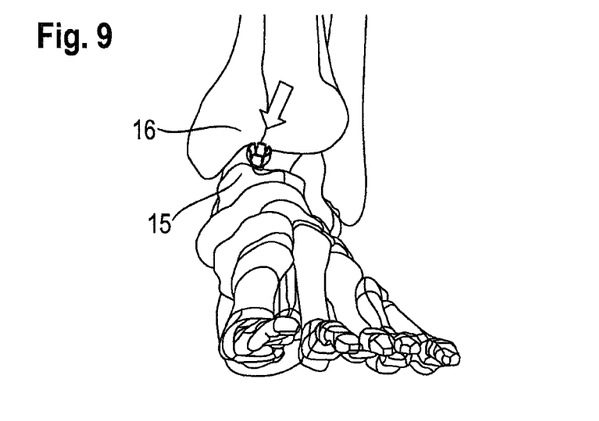
FIG. 9 shows the same as in FIG. 8, but in a front view.
Figure 10:
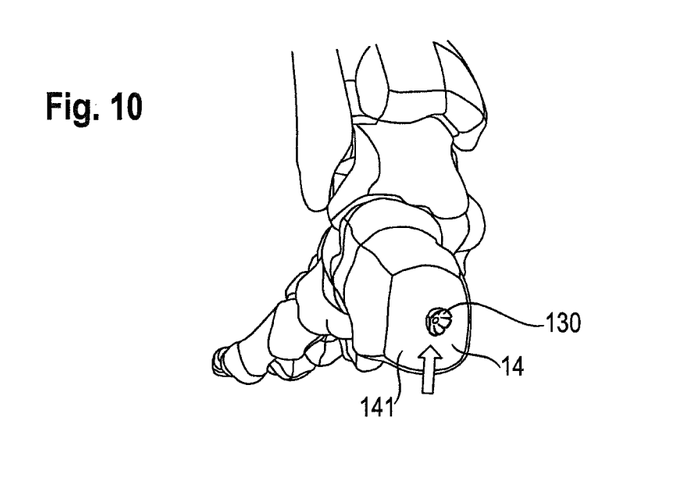
FIG. 10 shows the same as in FIG. 8, but in a back view.

While FIG. 8 shows a side view, FIGS. 9 and 10 show a front and backside view, respectively.

As shown in FIG. 11, Kirschner wires 18 indicated as dashed lines can be applied to reposition the bones or fragments of bones, respectively.

In a next step, shown in FIG. 12A, the heel is mounted to the main support 2 of the targeting device 1 between the two fixation devices 3, 4 such that ball heads 38, 47 face the respective tulip heads 130 of the bone anchors 13. It may be noted that the configuration allows the right foot to be installed on the device in the same manner as the left foot, i.e., in both cases the foot is mounted in a horizontal posture.

Further, vertical parts 39 and 45 of the first and second fixation devices 3, 4 respectively, provide a height to the pins 37, 46 and ball heads 38, 47, respectively, such that the pivoting plane of pivoting device 8, which is also the plane of the tube portion 12 and the arc-shaped bore to be drilled, intersects the bone assembly in a medial orientation, that allows the bore to securely extend through the calcaneus, talus and tibia. The height of pins 37, 46 or ball heads 38, 47 may differ from each other.

In this embodiment, the vertical height of pin 37 and ball head 38 of the first fixation device 3 with respect to a plane in which the three fixation devices 3, 4, 6 move and/or a plane in which the first and second pivotable support portions 5, 7 rotate or a plane in which the pivoting device 8 rotates (each of these planes being parallel to each other in this embodiment), is larger than the vertical height of pin 46 and ball head 47 of the second fixation device 4 by a specific distance in the vertical direction. This advantageously guarantees an inclination of the orientation of the foot and the bone assembly with respect to the plane of the arc-shaped bore to be drilled, when the bone anchors 13 are inserted, providing a most suitable position for the respective bones 14, 15 as shown in FIGS. 8-10.

Next, the tulip head 130 of the bone anchor 13 inserted into calcaneus 14 is snapped onto the ball head 47 of the second fixation device 4, see FIG. 12B. Then, the carriage 32 of the first fixation device 3 is moved towards the talus 15 such that the tulip head 130 of the bone anchor 13, which has been inserted into the talus 15, is snapped on the ball head 38 of the first fixation device 3. Then, the position of the carriage 32 along the guide rails 20, 21 is locked. At this stage, a 2-point fixation is achieved.

Next, as shown in FIG. 13, the Schanz screw 17 is transversally fixed into the tibia 15 and the first pivotable support portion 5 is attached to the first fixation device 3 provided at main support 2 and being rotatable around vertical axis 91. The third fixation device 6 is then slidably adjusted to receive a head portion of the Schanz screw 17. The receiving part 63 of the third fixation device 6 is locked and the position of the carriage 62 along the elongated rod 50 is locked as well. At this step, a 3-point fixation has been established.

As shown in FIG. 14, the second pivotable support portion 7 is attached to the main support 2 (see arrow C in FIG. 14), and the drill jig 10 with its tubular section 102 is mounted to the rotational support 72 of the second pivotable support portion 7. Then, the rotational position of the second pivotable support portion 7 is determined (see arrow D) by bringing the jig portion 101 of drill jig 10 in coincidence with a desired position for the bore within the bone assembly, by overlay of jig portion 101 over the heel (see arrow E). For this purpose, an X-ray tool allows the operator, or surgeon or others, to recognize the position of the respective bones, whereby the jig portion 102 and its scale are easily visible. The optional rib pattern at the bottom face of the carriage 42 allows for fine adjustment. Once the ideal rotational position has been determined, the second pivotable support portion 7 is locked.

As shown in FIG. 15, the drill jig 10 is removed and replaced (see arrow F) with the drill arrangement including drill tool 11 and tube portion 12 with the circular arc-shaped tubular body 125 and drill bit 126. Drill tool 11 is then operated to rotate drill bit 126 and pivoting device 8 is advanced clockwise (see arrow G). Drill bit 126 enters the calcaneus 14 through its end face.

As shown in FIG. 16, an end point is determined by a scale provided at the tube portion 12 in comparison with a determination that has been made based on the scale provided on the jig portion 101. Thereby, a circular arc-shaped bore has been cut into the calcaneus 14, through the talus 15 and into the tibia 16.

As shown in FIG. 17, the hindfoot is then removed from the frame and main portion, the anchors 13 and the Schanz screw 17 may also be removed and a nail 19 can be inserted into the circular arc-shaped bore thus formed.

The targeting device 1 or its components may be formed from any suitable material, in particular stainless steel, titanium, titanium alloys, or biocompatible plastic or elastomer materials, etc. Rubber or similar materials providing grip may also be used.

The targeting device 1 may also be provided as a kit in conjunction with the bone anchors 13 as described herein.

In the embodiment shown above, the tube portion 12 is designed to have a circular arc-shape. However, according to a modification, the arc-shape may also depart from being circular. For example, the radius of curvature $r_c$ may vary along the central axis of the tube portion 12 or may attain different values for specific segments of the same. According to another modification, the pivoting movement may be established by a combined translational (e.g., radial) and rotational movement of the tube portion 12 in order to achieve an arc-shaped bore hole.

In the embodiment above, the main support 2 is provided by two guide rails 20, 21. According to modifications, just one guide rail, or a larger platform may be provided, wherein the fixation devices may be adjusted by other means, e.g., by a ratchet, or a set of multiple fixing holes within the platform.

In the embodiment above, the first and second pivotable support portions 7, 8 are provided to be connected to the main support 2 via joints. However, according to modifications, the frame including main support 2, and the first and second pivotable support portions 7, 8 may also be provided as one single element, which allows translational or rotational positioning of the at least three fixation devices 3, 4, 6 on a common platform as described above.

In the embodiment above, the three fixation devices 3, 4, 6 are provided as parts separate from the main support 2. However, according to modifications, one or more of the fixation devices may also be provided as integral parts of the main support or frame, wherein the main support or frame as a whole allows for adjustment of the mutual distances between the fixation devices, or their mutual rotational positions.

In the embodiment above, specific arrangements for receiving portions and bone anchors have been described. However, according to modifications, it is also possible that other connection and fixation mechanisms are employed. For example, each of the at least three fixation devices may comprise a ball head connectable to a tulip head of a bone anchor. Likewise, the bone anchor may comprise the ball head and one or more of the fixation devices may include the tulip head. Further, one or more of the bone anchors may be connected to a rod or plate, where the rod or plate is received by the receiving portion of the respective fixation device.

Moreover, according to another modification, 4, 5, 6 or even more fixation devices may be provided on the targeting device 1.

In the embodiment above, a targeting device for drilling a bore in the human hindfoot is described in detail. However, the targeting device as proposed herein is also applicable to other parts of the human body. Moreover, the bore drilled using the targeting device does not necessarily require it to be provided with a nail. Rather, other applications such as forming an access to a specific part in front, within or behind any bone of the human body are also encompassed by the teaching as described herein.

The invention claimed is:

1. A targeting device for guiding a drill arrangement for forming an arc-shaped bore in a bone assembly comprising adjacent bones or bone fragments, the targeting device comprising:

a support frame comprising at least three fixators when assembled;

a pivoter configured to be mounted to the support frame and to receive the drill arrangement and to allow a pivoting movement of the drill arrangement along an arc-shaped path having a predetermined radius of curvature around a pivot axis when the drill arrangement is received in the pivoter;

wherein each of the at least three fixators is configured to fix to a bone or bone fragment of the bone assembly to define a fixed position of the bone assembly in space with respect to the pivoter when a foot comprising the bone assembly is positioned on the support frame; and wherein at least two of the at least three fixators are for fixing to the bone assembly in opposing directions when assembled on the support frame.

2. The targeting device of claim 1, wherein a first fixator and a second fixator of the at least three fixators are provided on a main support, which includes at least one guide configured to allow a slidable adjustment of a position of one fixators with respect to the other fixator.

3. The targeting device of claim 2, wherein the support frame comprises a first pivotable support portion configured to be rotatable within a single plane with respect to the main support, and a third fixator of the at least three fixators is configured to be slidable on the first pivotable support portion when the third fixator is not locked.

4. The targeting device of claim 3, wherein one or more of the at least three fixators comprises a receiving portion configured to receive a portion of a bone anchor configured to be anchored in a respective bone or fragment of the bone assembly.

5. The targeting device of claim 4, wherein the first and second fixators are each provided with a receiving portion shaped as a spherical ball and configured to cooperate as a snap-on mechanism with a hollow tulip head of a bone anchor.

6. The targeting device of claim 4, wherein the third fixator includes a receiving portion formed as a hole for receiving a rod-shaped head of a Schanz screw to be anchored into the bone.

7. The targeting device of claim 3, wherein the support frame comprises a second pivotable support portion;

the pivoter, is provided being rotationally supported on said second pivotable support portion;

wherein the second pivotable support portion is pivotable within a single plane with respect to the main support in order to adjust a position of the pivoter relative to the bone assembly, wherein an angular position of the second pivotable support portion with respect to the main support is lockable.

8. The targeting device of claim 7, wherein
the first pivotable support portion is configured to be connected to the first fixator and/or
the second pivotable support portion is configured to be connected to the second fixator.

9. The targeting device of claim 7, further comprising:
a drill jig for indicating a position of the circular arc-shaped bore, wherein the drill jig is configured to be rotationally supported on the second pivotable support portion.

10. The targeting device of claim 9, wherein
said drill jig comprises a portion having an arc-shape which has the radius of curvature configured to allow determination of a position with respect to the bone assembly of the arc-shaped bore to be drilled, when the foot comprising the bone assembly is positioned on the support frame.

11. The targeting device of claim 1, comprising:
the drill arrangement mountable on the pivoter, wherein the drill arrangement further comprises:
a drill device configured to provide a rotational movement;
a circular arc-shaped tubular body having an end connected to said drill device, and through which a means for transferring the rotational movement extends;
a drill bit provided at another end of the tubular body opposite to the end connected to the drill device, the drill bit being connected to the means for transferring the rotational movement such as to facilitate drilling into the bone assembly responsive to the rotational movement transferred from the drill arrangement when the drill arrangement is advanced into the bone when the pivoter is pivoted around the pivot axis.

12. The targeting device of claim 11, wherein:
the arc-shaped tubular body extends with the predetermined radius of curvature substantially along its entire length, wherein the arc-shape is circular.

13. The targeting device of claim 12, wherein:
when the drill arrangement is mounted to the targeting device, said circular arc-shaped tubular body is configured to extend within a plane that is defined by the at least three fixators.

14. The targeting device of claim 1, wherein
the radius of curvature is at least 130 mm.

15. The targeting device of claim 1, wherein
the radius of curvature is equal to or less than 240 mm.

16. The targeting device of claim 1, wherein the at least two of the at least three fixators are parallel to each other along their respective longitudinal axes when assembled on the support frame.

17. The targeting device of claim 1, wherein a first fixator of the at least three fixators is moveable toward a second of the at least three fixators.

18. The targeting device of claim 17, wherein a third fixator of the at least three fixators is moveable toward the second fixator.

19. A targeting device for guiding a drill arrangement for forming an arc-shaped bore in a bone assembly comprising adjacent bones or bone fragments, the targeting device comprising:
a support frame;
at least three fixators coupled to the support frame;
a drill arrangement pivotable along an arc-shaped path having a predetermined radius of curvature about a first pivot axis;
wherein each of the at least three fixators is configured to fix to a bone or bone fragment;
wherein at least a first and a second of said at least three fixators are for fixing to the bone assembly in opposing directions; and wherein a third of said at least three fixators is moveable relative to the first and second of said at least three fixators.

20. The targeting device of claim 19, wherein the first fixator is moveable toward the second fixator and wherein the third fixator is moveable toward the second fixator.

21. The targeting device of claim 20, wherein the third fixator is pivotable relative to the second fixator and translatable relative to the second fixator, and wherein the first fixator is translatable relative to the second fixator.

22. The targeting device of claim 19, further comprising a drill jig for being pivotable about said first pivot axis.

23. A method of using a targeting device for guiding a drill arrangement for forming an arc-shaped bore in a bone assembly comprising adjacent bones or bone fragments, the targeting device comprising a support frame provided with at least three fixators, wherein the support frame has a pivoter mounted to it and receiving the drill arrangement, wherein the drill arrangement is pivotable along an arc-shaped path having a predetermined radius of curvature around a pivot axis, the method comprising:
positioning a foot comprising the bone assembly on the support frame;
fixing a bone or bone fragment of the bone assembly with each of the at least three fixators by moving at least one of said at least three fixators toward another of said three fixators in order to define a fixed position of the bone assembly in space with respect to the pivoter;
receiving a drill arrangement at the pivoter; and
pivoting the drill arrangement along an arc-shaped path having a predetermined radius of curvature around the pivot axis to drill a bore.

24. The method of claim 23, wherein the at least two of the at least three fixators are parallel to each other along their respective longitudinal axes.

* * * * *

UNITED STATES PATENT AND TRADEMARK OFFICE
CERTIFICATE OF CORRECTION

PATENT NO.       : 9,592,064 B2                                             Page 1 of 1
APPLICATION NO. : 14/080782
DATED            : March 14, 2017
INVENTOR(S)      : Biedermann et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 319 days.

Signed and Sealed this
Twenty-fifth Day of September, 2018

Andrei Iancu
*Director of the United States Patent and Trademark Office*